United States Patent
Elder et al.

(10) Patent No.: US 9,575,051 B2
(45) Date of Patent: Feb. 21, 2017

(54) TEST STRIP CONNECTOR CONTACT PROTECTION

(71) Applicant: Cilag GmbH International, Zug (CH)

(72) Inventors: David Elder, Inverness (GB); Steven Setford, Inverness (GB); Allan Faulkner, Inverness (GB); Ryan Walsh, Douglassville, PA (US)

(73) Assignee: Cilag GmbH International, Zug (CH)

( * ) Notice: Subject to any disclaimer, the term of this patent is extended or adjusted under 35 U.S.C. 154(b) by 544 days.

(21) Appl. No.: 14/138,730

(22) Filed: Dec. 23, 2013

(65) Prior Publication Data
US 2015/0177174 A1    Jun. 25, 2015

(51) Int. Cl.
*G01N 27/327* (2006.01)
*G01N 33/487* (2006.01)
*A61B 5/145* (2006.01)

(52) U.S. Cl.
CPC ....... *G01N 33/4875* (2013.01); *A61B 5/14532* (2013.01); *G01N 27/3273* (2013.01)

(58) Field of Classification Search
CPC ..................................... G01N 27/327–27/3274
See application file for complete search history.

(56) References Cited

U.S. PATENT DOCUMENTS

| | | | |
|---|---|---|---|
| 3,585,570 A | 6/1971 | Jans | |
| 4,717,546 A * | 1/1988 | Barnett | G01N 27/3271 422/63 |
| 5,120,420 A | 6/1992 | Nankai et al. | |
| 6,180,063 B1 | 1/2001 | Markart | |
| 6,673,627 B2 | 1/2004 | Tyrrell et al. | |
| 6,893,545 B2 | 5/2005 | Gotoh et al. | |
| 7,198,606 B2 | 4/2007 | Boecker et al. | |
| 7,896,703 B2 | 3/2011 | Stafford et al. | |
| 8,475,732 B2 | 7/2013 | Simmons et al. | |
| 8,535,619 B2 | 9/2013 | Zocchi | |
| 2007/0249921 A1 | 10/2007 | Groll et al. | |
| 2009/0301899 A1 | 12/2009 | Hodges et al. | |
| 2011/0040164 A1 | 2/2011 | Galasso | |
| 2011/0208435 A1 | 8/2011 | Elder et al. | |
| 2012/0100601 A1 | 4/2012 | Simmons et al. | |

FOREIGN PATENT DOCUMENTS

| | | |
|---|---|---|
| CN | 101490546 A | 7/2009 |
| FR | 2330161 | 5/1977 |
| JP | 2012095949 A | 5/2012 |
| WO | 2006070199 | 7/2006 |
| WO | 2008088333 | 7/2008 |

(Continued)

OTHER PUBLICATIONS

"Decentralized Electrochemical Monitoring of Trace Metals: From Disposable Strips to Remote Electrodes", Plenary Lexture, Analyst, May 1994, vol. 119, pp. 763-766.

(Continued)

*Primary Examiner* — J. Christopher Ball

(57) ABSTRACT

A test strip port connector of a test meter receives an analytical test strip comprising a sample chamber for receiving a fluid sample. The fluid sample is prevented from contaminating an interior region of the test strip port connector by a sealing mechanism having a seal configured to be moved into a sealing position across the test strip.

5 Claims, 6 Drawing Sheets

(56) References Cited

FOREIGN PATENT DOCUMENTS

| | | |
|---|---|---|
| WO | 2012131312 | 10/2012 |
| WO | 2013012938 | 1/2013 |
| WO | 2013066362 A1 | 5/2013 |
| WO | 2013079977 | 6/2013 |

OTHER PUBLICATIONS

International Search Report and Written Opinion issued in related International Patent Application No. PCT/US2014/071806, mailed Apr. 30, 2015, 18 pages.

\* cited by examiner

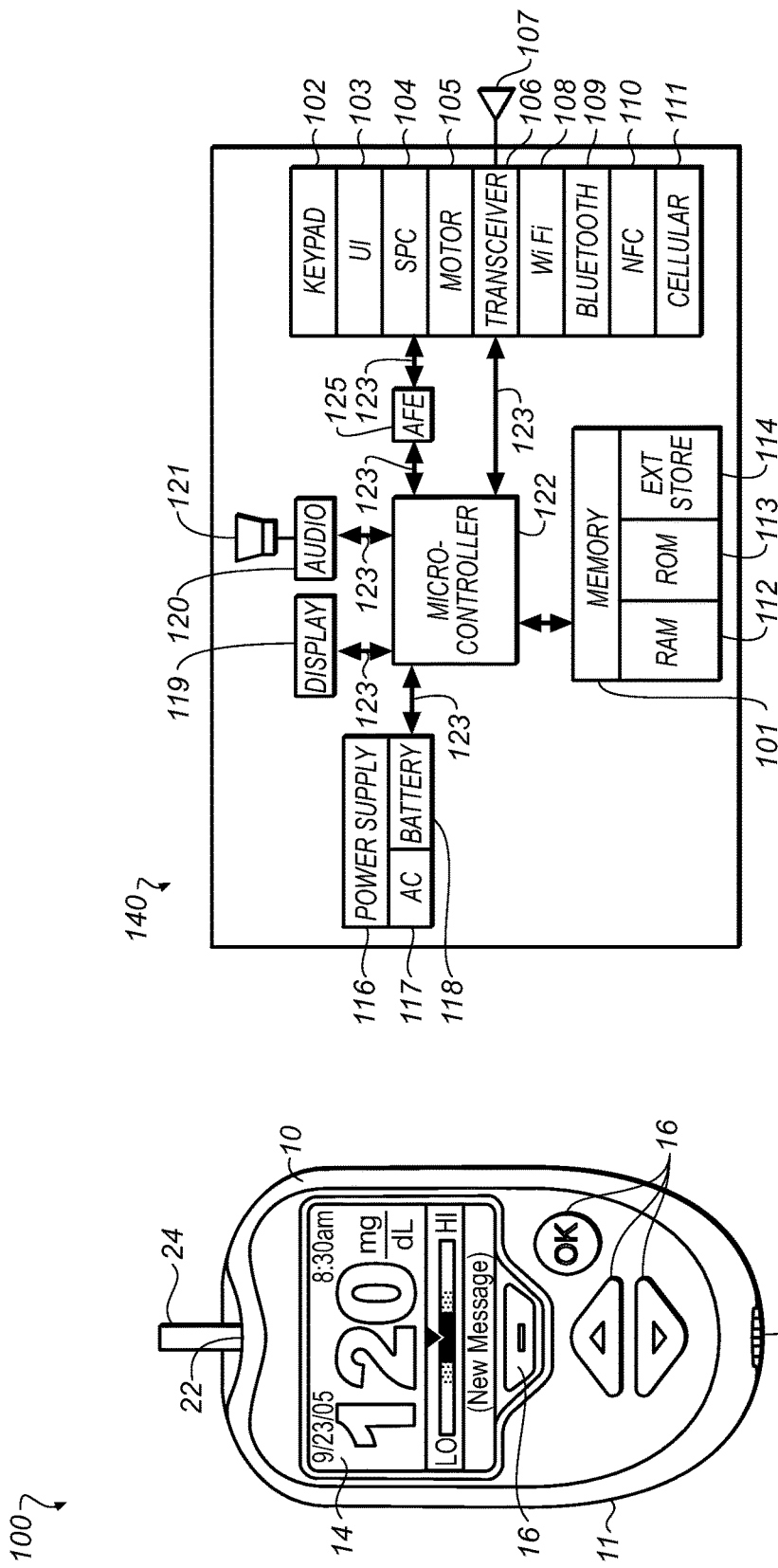

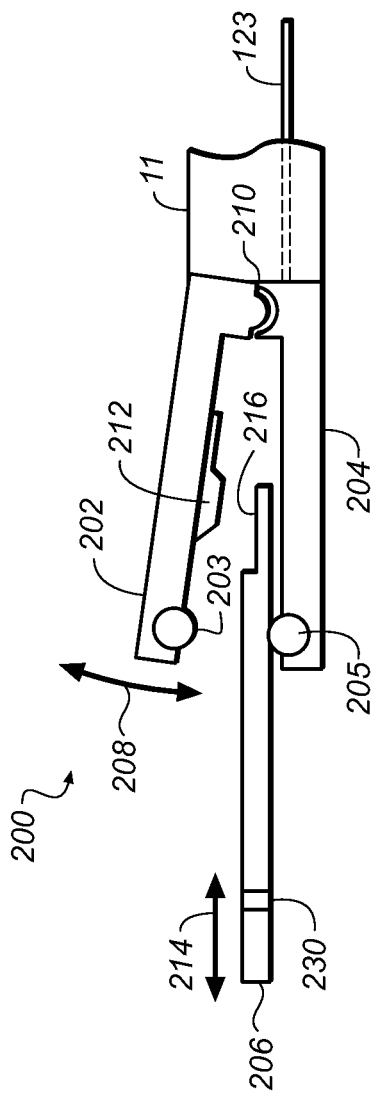
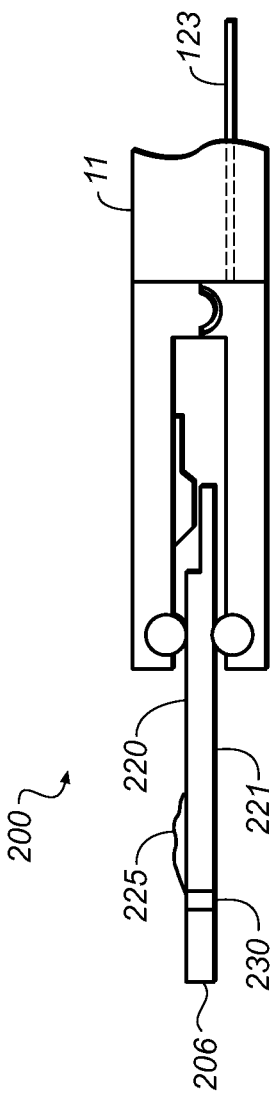
FIG. 2A
FIG. 2B

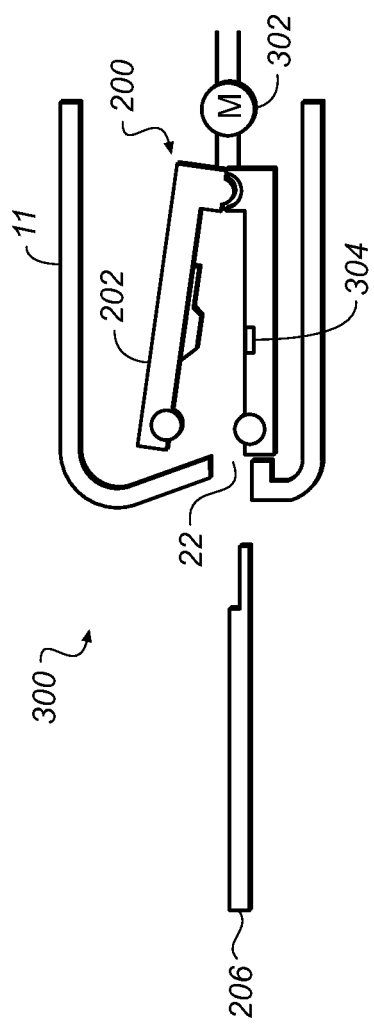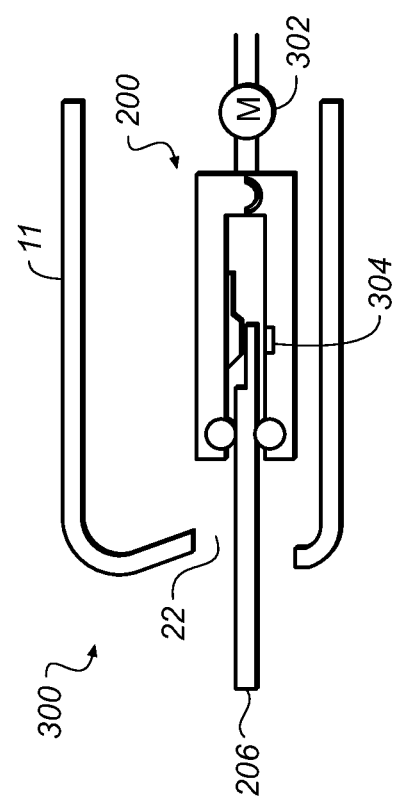
FIG. 3A
FIG. 3B

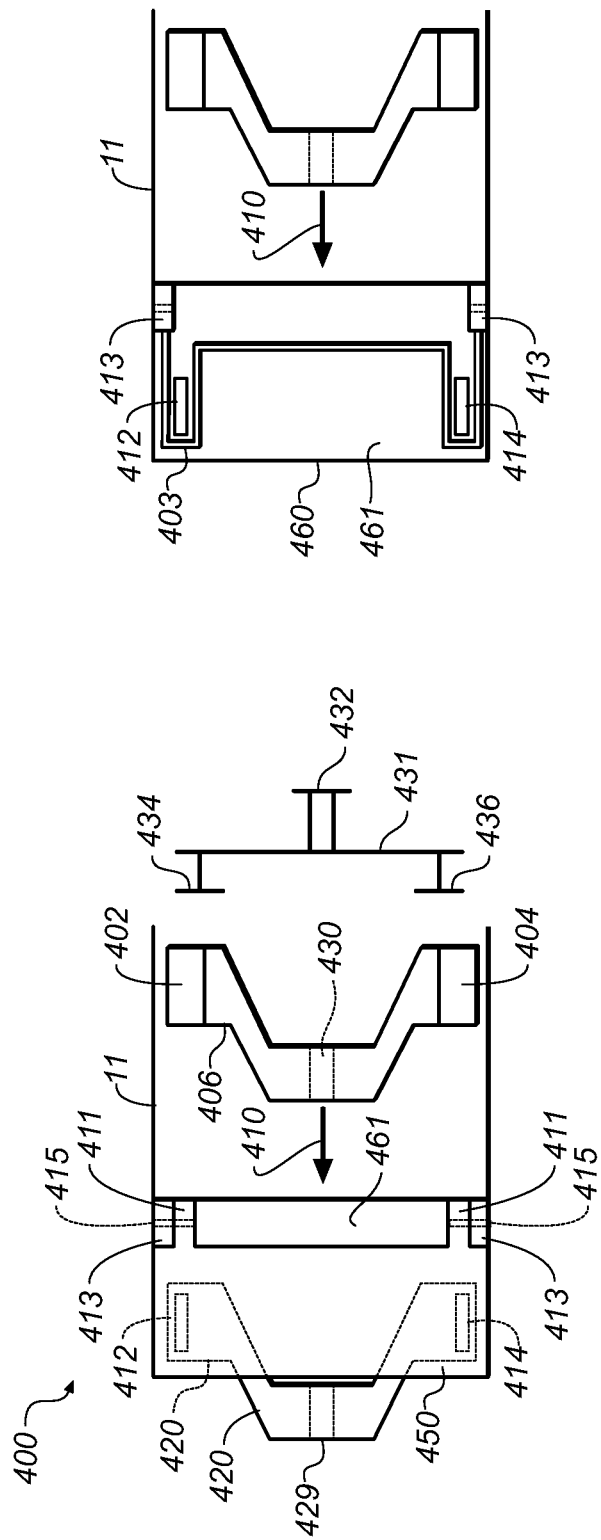

TEST STRIP CONNECTOR CONTACT PROTECTION

TECHNICAL FIELD

This application generally relates to the field of analyte measurement systems and more specifically to a test meter comprising a seal guard for preventing ingress of sample fluid and other contaminants.

BACKGROUND

Systems that measure analytes in biological fluids, as exemplified by the determination of glucose in blood, typically comprise a test meter that is configured to receive a biosensor, usually in the form of an analytical test strip. Because many of these measurement systems are portable, and testing can be completed in a short amount of time, patients are able to use such devices in the normal course of their daily lives without significant interruption to their personal routines. For example, a person with diabetes may measure their blood glucose levels several times a day as a part of a self management process to ensure glycemic control of their blood glucose within a target range.

There currently exist a number of available portable electronic devices that can measure glucose levels in an individual based on a small sample of blood. A test strip is inserted into a test strip port of the meter, which includes a test strip port connector that mechanically and electrically engages the inserted test strip. To initiate an assay of a sample, a person is required to prick their finger using a lancet or similar device and provide a blood sample onto the test strip. Test strips oftentimes may be difficult to manipulate by users due to the small size and geometry of the test strips and limitations in the manual dexterity of some users. The user needs to properly apply a sample onto a specified area of the test strip such that the applied sample enters a sample chamber wherein an assay sequence is undertaken electronically by the meter. It is important for the electrical connections between the meter and the test strip to remain clean and unimpeded by contaminants, such as sample fluid. Fluidic interference from the sample will cause the electronic circuitry to misread the analyte concentration of the provided sample and can also affect the working life of the test meter. Hence, proper electrical engagement and communication between the test strip and the analyte meter will be insured if fluid ingress from the sample or other contaminant is prevented from entering the meter through the test strip port connector. It would therefore be advantageous to provide a test meter that includes features to block or otherwise prevent fluidic ingress.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 1A illustrates a diagram of an exemplary analyte measurement system, including a test meter and an analytical test strip;

FIG. 1B illustrates a diagram of an exemplary processing system of the test meter of FIG. 1A;

FIGS. 2A-2B illustrate respective side views, taken in section, of an exemplary test strip port connector of a test meter, which includes a movable portion that selectively opens and closes to permit and deny access to the interior of the test strip port connector of the test meter of FIG. 1A;

FIGS. 3A-3B illustrate respective side views of another exemplary test strip port connector of a test meter having a movable portion that selectively opens and closes to permit and close access to the interior of the test strip port connector of the test meter of FIG. 1A;

FIG. 4A illustrates a top plan view of another embodiment of a test strip port connector for receiving test strips that are individually dispensed thereto inside the test meter housing;

FIG. 4B illustrates a top facing view of a bottom member of the test strip connector of FIG. 4A;

DETAILED DESCRIPTION

Figure 4C:
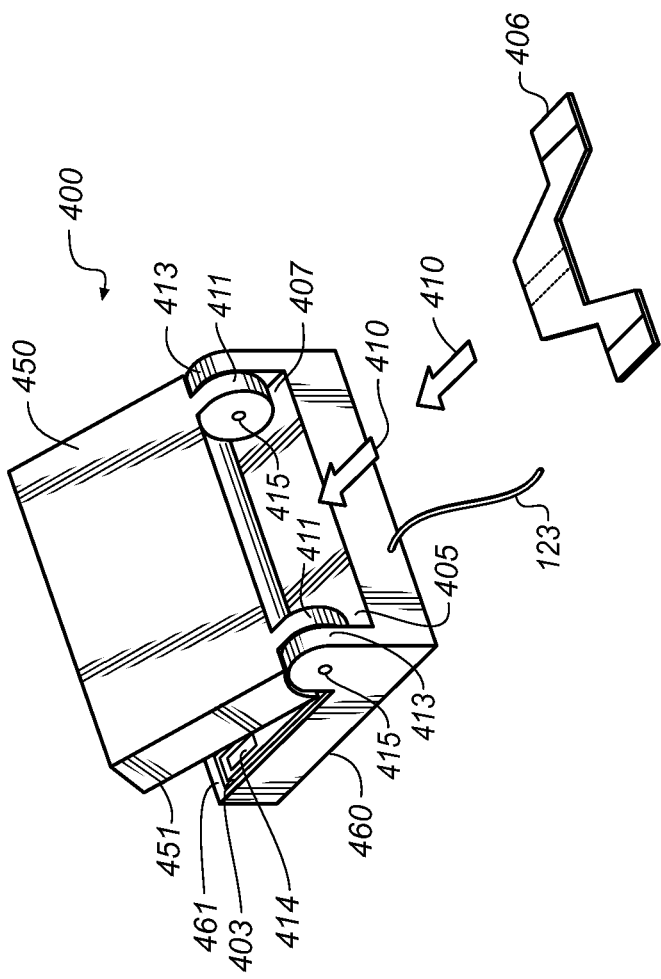
FIG. 4C illustrates a perspective view of the test strip connector of FIGS. 4A-4B.

The following description relates to an analyte test meter and more specifically embodiment are discussed in detail that pertain to a test strip connector that is configured with a compliant seal guard to prevent the ingress of contaminants into the meter. Throughout the discussion that follows, several terms are used in order to provide a suitable frame of reference in regard to the accompanying drawings. These terms, which can include "top", "bottom", "first", "second", "above", "below", "front", "back" and the like are not intended to change the intended scope of the inventive concepts discussed, including the appended claims, except where specifically expressed. The embodiments that follow are specific to a blood glucose measurement meter and system, but it will be readily apparent that the concepts discussed would be applicable to other systems and/or meters. In this regard, the detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "patient" or "user" refer to any human or animal subject and are not intended to limit the systems or methods to human use, although use of the subject invention in a human patient represents a preferred embodiment.

The term "sample" means a volume of a liquid, solution or suspension, intended to be subjected to qualitative or quantitative determination of any of its properties, such as the presence or absence of a component, the concentration of a component, e.g., an analyte, etc. The embodiments of the present invention are applicable to human and animal samples of whole blood. Typical samples in the context of the present invention as described herein include blood, plasma, serum, suspensions thereof, and haematocrit.

The term "about" as used in connection with a numerical value throughout the description and claims denotes an interval of accuracy, familiar and acceptable to a person skilled in the art. The interval governing this term is preferably +10%. Unless specified, the terms described above are not intended to narrow the scope of the invention as described herein and according to the claims.

With reference to FIG. 1A there is illustrated an analyte measurement system 100 that includes an analyte test meter 10 and a test strip 24 that is used with the test meter 10. The analyte test meter 10 is defined by a housing 11 that includes a test strip port opening 22 for receiving one end of the test strip 24. Within the housing 11 proximate the test strip port opening 22 there is disposed a test strip port connector having various exemplary embodiments as described herein. The test strip port connector mechanically and electrically engages the test strip 24 when inserted therein. As noted above and according to this exemplary embodiment, the analyte test meter 10 is a blood glucose meter and the test strip is provided in the form of a glucose test strip 24 which can be inserted into the test strip port opening 22 for performing blood glucose measurements. The analyte meter 10 further includes a plurality of user interface buttons, or keypad, 16 and a display 14, each disposed on a front facing side of the housing 11 as well as a data port 13, as illustrated in FIG. 1A, disposed on a bottom facing side of the housing 11 and opposite the test strip port opening 22, according to this exemplary embodiment. The positioning of the foregoing features of the test meter 10 can easily be varied. A predetermined number of glucose test strips 24 may be stored in the housing 11 and made accessible for use in blood glucose testing. In one embodiment described herein, the test strips 24 may be stored in a dispenser within the housing 11 that internally dispenses individual test strips 24 into the test strip port connector.

The plurality of user interface buttons 16 can be configured to allow the entry of data, to prompt an output of data, to navigate menus presented on the display 14, and to execute commands. Output data can include, for example, values representative of an analyte concentration that are presented on the display 14. User inputs may be requested via programmed prompts presented on the display 14, and a user's responses thereto may initiate command execution or may include data that may be stored in a memory module of the analyte meter 10. Specifically, and according to this exemplary embodiment, the user interface buttons 16 include markings, e.g., up-down arrows, text characters "OK", etc, which allow a user to navigate through the user interface presented on the display 14. Although the buttons 16 are shown herein as separate switches, a touch screen interface on display 14 with virtual buttons may also be utilized. The display 14 may comprise a movable type of display, such as a sliding display, a hinged display or a tiltable display.

The electronic components of the glucose measurement system 100 can be disposed on, for example, a printed circuit board situated within the housing 11 and forming a data management unit 140 of the herein described system 100. FIG. 1B illustrates, in simplified schematic form, several of the electronic subsystems disposed within the housing 11 for purposes of this embodiment. The data management unit 140 includes a processing unit 122 in the form of a microprocessor, a microprocessor block such as in the form of a chipset, a microcontroller, an application specific integrated circuit ("ASIC"), a mixed signal processor ("MSP"), a field programmable gate array ("FPGA"), or a combination thereof, and is electrically connected to various electronic modules included on, or connected to, the printed circuit board, as will be described below.

According to this exemplary embodiment, the processing unit 122 is electrically connected to a test strip port connector ("SPC") circuit 104, that is accessible via the test strip port opening 22, and which is operated by an analog front end (AFE) subsystem 125. The analog front end subsystem 125 is electrically connected to the SPC circuit 104 during blood glucose testing. To measure a selected analyte concentration, the SPC circuit 104 detects a resistance, or impedance, across electrodes of the analyte test strip 24 having a blood sample disposed in a sample chamber therein, using a potentiostat, or transimpedance amplifier, and converts an electric current measurement into digital form for presentation on the display 14, typically in units of milligrams per deciliter or millimoles per liter (mg/dl or mmol/1). The processing unit 122 can be configured to receive input from the SPC circuit 104 via analog front end subsystem 125 over an interface 123 and may also perform a portion of the potentiostat function and the current measurement function.

The analyte test strip 24 according to this embodiment is in the form of a glucose test strip comprising an electrochemical cell, or sample chamber. The test strip 24 is defined by one or more nonporous non-conducting substrates, or layers, onto which one or more electrodes, or conductive coatings may be deposited. These electrodes may function as working electrodes, reference electrodes, counter electrodes or combined counter/reference electrodes. Additional non-conducting layers may be applied in order to define the planar dimensions of the electrode structure(s). The test strip 24 can also include a plurality of electrical contact pads, where each electrode can be in electrical communication with at least one electrical contact pad. The strip port connector 104 can be configured to electrically interface to the electrical contact pads, using electrical contacts in the form of flexible conductive prongs, and form electrical communication with the electrodes and, thereby, with the electrochemical cell. Test strip 24 further includes a reagent layer that is disposed over one or more electrodes within the test strip 24, including the working electrode. The reagent layer can include an enzyme and a mediator. Exemplary enzymes suitable for use in the reagent layer include glucose oxidase, glucose dehydrogenase (with pyrroloquinoline quinone co-factor, "PQQ"), and glucose dehydrogenase (with flavin adenine dinucleotide co-factor, "FAD"). Enzymes other than those used to determine glucose are also applicable, for example, lactate dehydrogenase for lactate, β-hydroxybutyrate dehydrogenase for β-hydroxybutyrate (ketone body). An exemplary mediator suitable for use in the reagent layer includes ferricyanide, which in this case is in the oxidized form. Other mediators may be equally applicable, depending upon the desired strip operating characteristics, for example, ferrocene, quinone or osmium-based mediators. The reagent layer can be configured to physically transform glucose into an enzymatic by-product and in the process generate an amount of reduced mediator (e.g., ferrocyanide) that is proportional to the glucose concentration. The working electrode can then be used to measure a concentration of the reduced mediator in the form of a current magnitude. In turn, microcontroller 122 can convert the current magnitude into a glucose concentration whose numerical value (in mg/dl or mmol/l) may be presented on the display 14. An exemplary analyte system, including other test strip and meter details, may be found in U.S. Patent Application Publication No. US 2009/0301899 A1 entitled "System and. Method for Measuring an Analyte in a Sample", which is incorporated by reference herein as if fully set forth in this application.

Still referring to FIG. 1B, the display module 119, which may include a display processor and display buffer, is electrically connected to the processing unit 122 over the communication interface 123 for receiving and displaying output data, and for displaying user interface input options under control of processing unit 122. The structure of the user interface, such as menu options, is stored in user interface module 103 and is accessible by processing unit 122 for presenting menu options to a user of the blood glucose measurement system 100. An audio module 120 includes a speaker 121 for outputting audio data received or stored by the DMU 140. Audio outputs can include, for example, notifications, reminders, and alarms, or may include audio data to be replayed in conjunction with display data presented on the display 14. Such stored audio data can be accessed by processing unit 122 and executed as playback data at appropriate times. User input module 102 receives inputs via user interface buttons 16 which are processed and transmitted to the processing unit 122 over the communication interface 123. The processing unit 122 may have electrical access to a digital time-of-day clock connected to the printed circuit board for recording dates and times of blood glucose measurements, which may then be accessed, uploaded, or displayed at a later time as necessary.

A memory module 101, that includes but are not limited to volatile random access memory ("RAM") 112, a non-volatile memory 113, which may comprise read only memory ("ROM"), non-volatile RAM ("NVRAM"), or flash memory, and a circuit 114 for connecting to an external portable memory device via a data port 13, is electrically connected to the processing unit 122 over a communication interface 123. External memory devices may include flash memory devices housed in thumb drives, portable hard disk drives, data cards, or any other form of electronic storage devices. The on-board memory can include various embedded applications executed by the processing unit 122 for operation of the analyte meter 10, as will be explained below. On board memory can also be used to store a history of a user's blood glucose measurements including dates and times associated therewith. Using the wireless transmission capability of the analyte meter 10 or the data port 13, as described below, such measurement data can be transferred via wired or wireless transmission to connected computers or other processing devices. A motor control module 105 may include a motor control circuit for supplying voltage signals to a motor contained within the housing 11 of the herein described analyte measurement system 100. The processing unit 122 may communicate motor activation signals to the motor control module 105 which are then executed via appropriate voltage signals transmitted to an an-board motor for activating various mechanical functions performed by the test meter 10, for example, as described herein, a motor may be used to activate a member in a test trip port connector to seal it against fluidic ingress by a fluid sample. The motor control module 105 may implement an analog voltage control circuit, a quadrature signal control circuit, or a digital pulse-width-modulated (PWM) motor control signal.

A wireless module 106 may include transceiver circuits for wireless digital data transmission and reception via one or more internal antennas 107, and is electrically connected to the processing unit 122 over communication interface 123. The wireless transceiver circuits may be in the form of integrated circuit chips, chipsets, programmable functions operable via processing unit 122, or a combination thereof. Each of the wireless transceiver circuits is compatible with a different wireless transmission standard. For example, a wireless transceiver circuit 108 may be compatible with the Wireless Local Area Network IEEE 802.11 standard known as WiFi. Transceiver circuit 108 may be configured to detect a WiFi access point in proximity to the analyte meter 10 and to transmit and receive data from such a detected WiFi access point. A wireless transceiver circuit 109 may be compatible with the Bluetooth protocol and is configured to detect and process data transmitted from a Bluetooth hub in proximity to the analyte meter 10. A wireless transceiver circuit 110 may be compatible with the near field communication ("NFC") standard and is configured to establish radio communication with, for example, an NFC compliant reader device in proximity to the analyte meter 10. A wireless transceiver circuit 111 may comprise a circuit for cellular communication with cellular networks and is configured to detect and link to available cellular communication towers.

A power supply module 116 is electrically connected to all modules in the housing 11 and to the processing unit 122 to supply electric power thereto. The power supply module 116 may comprise standard or rechargeable batteries 118 or an AC power supply 117 may be activated when the analyte meter 10 is connected to a source of AC power. The power supply module 116 is also electrically connected to processing unit 122 over the communication interface 123 such that processing unit 122 can monitor a power level remaining in a battery power mode of the power supply module 116.

In addition to connecting external storage for use by the analyte meter 10, the data port 13 can be used to accept a suitable connector attached to a connecting lead, thereby allowing the analyte meter 10 to be connected to an external device such as a personal computer. Data port 13 can be any port that allows for transmission of data, power, or a combination thereof, such as a serial, USB, or a parallel port.

With reference to FIGS. 2A-2B, there is illustrated a side view of an exemplary test strip port connector 200 for the analyte meter 10 wherein a test strip 206 is being inserted and subsequently removed according to the directions indicated by the double-sided arrow 214. In this embodiment, the test strip port 200 comprises top and bottom members 202, 204, respectively, each connected to one another by a hinge 210 disposed at one end of the test meter housing 11. According to this exemplary embodiment, the test strip 206 comprises electrical contact pads 216 at a first end of the test strip 206 that is configured and sized for insertion into the test strip port 200. The contact pads 216, which include at least two contact pads, may be disposed on a top surface of the test strip 206, as illustrated, or on a bottom surface of the test strip 206, or a combination thereof. The sample chamber 230, or electrochemical cell, of the herein described test strip 206 is disposed proximate a second end of the test strip 206, opposite the first end. The sample chamber 230 is accessible to the user at a position exterior to the test strip port 200 to enable receipt of a blood sample applied by the user of the test meter 10. After the user applies a sample to the sample chamber 230, the sample is detected by the SPC circuit 104 and an assay sequence is initiated by the processing unit 122 as in the usual course.

Still referring to FIGS. 2A-2B, and according to this exemplary embodiment, the top and bottom members of the port define an interior enclosure in which the top member 202 can be moved in relation to the bottom member 204, the latter being fixed either as an integral part of the housing 11 or as a separate component. Movement of the top element 202 of the port 200 in an upward direction as indicated by the double-sided arrow 208 permits access to the defined interior enclosure by the test strip 206, as more specifically shown in FIG. 2A. The test strip 206 can then be inserted therein by the user and is placed at an assay position in the test strip port 200 when the test strip contact pad, or pads, 216 are in position to make an electrical connection with at least two electrical contacts 212, each corresponding to one of the contact pads 216, including at least one contact provided on the interior surface of the top member 202, in which the contact is engaged only upon closing the top member 202. As noted, the second end of the test strip, including the portion comprising the sample chamber 230, remains exterior to the strip port 200 in order to provide access to the sample chamber 230 by a user of the test meter 10 in order to introduce a sample therein.

Still referring to FIGS. 2A and 2B, and according to this embodiment, each of the unhinged ends of the top and bottom members 202, 204, forming the entrance of the port are each provided with seal members, including respective top and bottom contact seals 203, 205. Upon closing the top member 202, as illustrated in FIG. 2B, which may be manually performed by moving the top member 202 downwardly as indicated by the double-sided arrow 208, the top contact seal element 203 of the top member 202 is configured to engage and press against the top surface of the inserted test strip at an intermediate axial portion thereof. A corresponding bottom contact seal element 205, which is generally fixed, is disposed directly opposite the top contact seal element 203 to form a mating contact therewith, which also presses against the bottom surface of the test strip 221 so that the test strip 206 is pinched between the contact seal elements 203, 205, as illustrated in FIG. 2B, to prevent fluid 225 ingress from an exterior side of the contact seals 203, 205, into an interior side of the contact seals 203, 205. The contact seal elements 203, 205 are formed from a fluid-impermeable material that is preferably compliant, such as rubber or other elastomer. According to this embodiment, the contact seal elements are disposed in corresponding grooves which are formed in the top and bottom members 202, 204, wherein the grooves can include a curvature matching that of the contact seal elements 202, 204. The seal elements 203, 205, can have any suitable configuration (e.g., circular, polygonal) provided a suitable fluidic seal is formed when the top and bottom members 202, 204, are closed. The seal elements 203, 205 may deform slightly upon contacting each other and upon making contact with the test strip 206.

As noted and simultaneously with forming a seal between contact seal elements 203, 205, the electrical contacts 212 on the interior side of the top port member electrically engages the contact pads 216 of the test strip 206 when the top port member 202 is moved into the closed position. Thus, a fluid sample may be applied to the sample chamber 230 while any leakage or misapplication of the sample 225 is prevented from reaching an interior of the test strip port connector 200, and so cannot interfere with electrical signals communicated between the electrical contacts 212 of the test strip port 200 and the contact pads 216 of the test strip 206. In addition to providing protection from fluid ingress into the sample chamber, the contact seals 203, 205, also assist in fixing the test strip in a proper position, as shown in FIG. 2B, for the test meter 10 to perform an assay, as in the usual course, after a sample is provided in sample chamber 230.

Another embodiment of a test strip port connector 300 is described with references to FIGS. 3A-3B in which the test strip port connector 200 is enclosed within the test meter housing 11 proximate the test strip port opening 22 of the test meter 10. In this specific embodiment, the test strip port connector 200 is identical in operation to the embodiment described above in relation to FIGS. 2A-2B. However, and because the top member cannot be accessed manually, as in the prior embodiment, the strip port connector 200 further includes a motor 302 connected thereto and operated by control signals transmitted by the processing unit 122 via the motor control module 106 for opening and closing the top member 202 of the test strip port connector 200. The motor 302 may include other types of actuators such as a stepper motor, a miniature d.c. motor, a linear motor, a solenoid, or a shape memory alloy. In this embodiment, the top member 202 may remain in a (default) open position, as shown in FIG. 3A, when the test meter 10 is in a sleep state, and may move into a closed position, as shown in FIG. 3B, after a test strip 206 is inserted therein. The motor 302 may be activated to close the top port member 202 by the user pressing one of the buttons 16 which issues a signal to the processing unit 122 to activate the motor. In one embodiment, the test strip port connector 200 may include a detector 304 disposed therein for detecting an insertion of the test strip 206. Such a detector may be comprised of a mechanically activated switch, a photodiode based emitter/detector pair, or other types of detection mechanism that, upon being triggered by an inserted test strip 206, transmits a signal to the processing unit 122. Upon receiving the signal, the processing unit 122 may activate the motor 302 to close the top port member 202 onto the test strip 206. Similar to the operation of the embodiment described in relation to FIGS. 2A-2B, a portion of the test strip 206, including the sample chamber 230, or electrochemical cell, remains accessible to the user at a position exterior to the test strip port connector 300 so that the sample chamber 230 may receive a sample provided thereto by the user of the test meter 10, and the assay sequence may be initiated, as in the usual course.

It will be understood that the form of test strip and test meter used herein can be varied. For example, and with reference to FIGS. 4A-4C, there is illustrated another embodiment of a test strip port connector 400 that is configured to receive another exemplary test strip 406. In this specific embodiment, and rather than an axially defined substrate having first and second axial ends, the test strip 406 comprises contact pads 402, 404, at opposite lateral ends of the test strip 406 and in which the sample chamber 430 is disposed proximate a central portion of the test strip 406. An example of a test strip having this form of design is described in greater detail in United States Application Publication No. 2012-0267245-A1, the entire contents of which are herein incorporated by reference.

The test strip port connector 400 comprises a movable top port member 450 and a stationary bottom port member 460 hingably connected by hinge portions 411, 413 disposed in spaced relation at an interior side of the port connector 400. According to this specific embodiment, the hinge portion 411 is integrally formed with the top port member 450 while hinge portion 413 is integrally formed with the stationary bottom port member. The hinge portions 411, 413 may be rotatably linked together by a pin 415 (shown in phantom in FIG. 4A) extending through both hinge portions 411, 413 in a position coincident with a hinge axis about which the top port member 450 is rotated. A set of electrical contacts 412, 414 are disposed on a top surface 461 of the bottom member 460, which faces the bottom surface 451 of the top port member 450 when the test strip port connector 400 is closed. Alternatively, the electrical contacts 412, 414 may be appropriately disposed on an interior or bottom surface 451 of the top port member 450. Similarly, the test strip 406 may include contact pads 402, 404, correspondingly on an upper or lower surface thereof. In either embodiment, the electrical contacts 412, 414, are suitably positioned to electrically engage test strip contact pads 412, 404, respectively, when the top port member 450 is closed upon the fixed bottom port member 460. Similar to the embodiments described hereinabove, the top port member 450 is engaged by the user or a motor (not shown) to selectively open and close the port connector 400.

FIG. 4B represents a top view of the bottom port member 460 which includes a seal element 403 at the opening end thereof. The flexible elongated seal element 403 according to this embodiment is disposed within the top surface 461 of the bottom member 460 and is configured to surround the electrical contacts 412, 414. Although not shown, an identical, and similarly disposed, corresponding seal element may be placed in the bottom, or interior surface, 451 of the top port member 450 so that substantially the entire length of the seal element 403 meets and creates a sealing contact area with a mating surface of the seal element in the top port member 450. The seal element 403 is adhered, press fitted or otherwise disposed in a groove in the bottom port member 460, as is the seal element in the top port member 450 similarly adhered, press fitted or otherwise disposed in a groove in the top port member 450. These seal elements comprise characteristics similar to those of the seal elements 203, 205 in the embodiment of FIGS. 2A-2B. That is, the seal elements may be made of a pliable, compliant rubber or similar material that is fluid impermeable and at least a portion of its cross section may comprise a curved mating surface such as a circular cross-section. The mating seal elements of the top and bottom members 450, 460, pinch therebetween the portions of the test strip 406 proximate the contact pads 412, 414 to prevent fluidic ingress at the electrical contacts 412, 414, of any sample fluid that may travel along the test strip away from the sample chamber 430. As explained hereinabove, the mating seal elements also serve to secure the test strip 406 in the assay position 420 (FIG. 2A) wherein the sample chamber inlet 429 is exposed and accessible for receiving a sample outside the test strip port connector 400.

The architecture of the test strip port connector 400 permits a plurality of test strips to be supplied thereto from a storage location behind the test strip port connector 400, as shown in perspective in FIG. 4C. The test strip 406 may be inserted into the test strip port connector 400, when in the open position, by insertion through slotted portions 405, 407, and the space at the rearward side of, and between, the top and bottom port members 450, 460, as indicated by the arrows 410 of FIG. 4C. The test strip 406 is urged from an initial storage position within the housing 11 of the test meter 10 through the test strip port connector 400 toward its assay position 420 by use of a substantially rigid test strip slider 431 (FIG. 4A). The test strip slider 431 includes arms 434, 435 that may make contact with the portions of the test strip 406 proximate the contact pads 402, 404, respectively, as the slider 431 is manually urged in the direction 410 by a user of the test meter 10. The slider 431 may include a button, or tab, 432 accessible outside the housing 11 of the test meter 10 so that the user may apply finger pressure thereto to cause the slider 431 to slide forward in the direction of arrow 410, contact the test strip 406 and push it forward from a storage position within the test meter housing 11 through the strip port connector 400 and into the assay position 420, whereupon the slider button 432 may be released. This insertion mechanism may also be automated such as by manual or automatic activation of a motorized insertion mechanism or similar linear actuator. Upon releasing the button 432 after the test strip 406 reaches the assay position 420, the top member 450 may be closed to secure the test strip 406 at the assay position 420. A plurality of test strips 406 may be stored within the test meter housing 11 such as in a stack formation, wherein with each release of the button 432, another test strip 406 is pushed to the top of the stack, such as by a spring loaded mechanism, whereby the test strip slider 431 may again be operated by the user to dispense another test strip 406 into an assay position in the test strip port connector 400 once again.

A person skilled in the art will appreciate that the test strip port connector embodiments 200, 300, 400, described herein can have various configurations other than those shown, and may include any combination of features disclosed herein and known in the art. For example, the top member 202, 450 of the test strip port connectors 200, 300, 400, may be opened or closed manually or in a motorized fashion in any of the embodiments disclosed herein. Similarly, the bottom member of the test strip port connector may be movable rather than the top member as described in the exemplary embodiments herein, or both top and bottom members may be movable in combination. The test strip 206, 406 may also comprise various shapes other than the embodiments described herein. Moreover, each test strip 206, 406, may include a sample chamber at various locations for measuring the same (glucose) and/or different analytes in a sample. The test strip 206, 406 is typically in the form of rigid, semi-rigid, or flexible layers having sufficient structural integrity to allow handling and connection to the test strip port connector embodiments 200, 300, 400, and may comprise two or more electrical contact pads on a common surface, on opposing surfaces, at the same or opposite ends of the test strip, or combinations thereof. Therefore, the strip port connector embodiments 200, 300, 400 will comprise electrical contacts each appropriately positioned to engage one of the contact pads.

Figure 5:
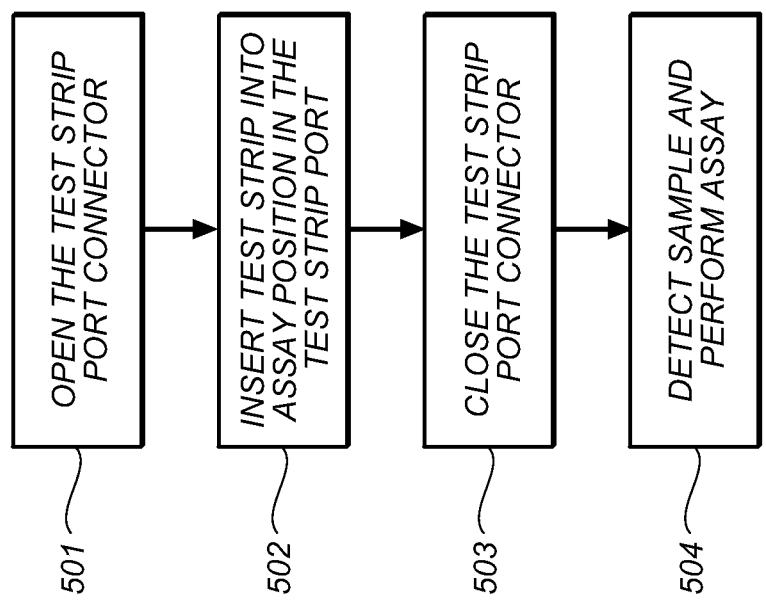
FIG. 5 illustrates a flow chart of exemplary steps performed by a test meter having the test strip port connectors of FIGS. 2A-4C.

With reference to FIG. 5, there is illustrated a flowchart illustrating exemplary steps performed in using a test strip port connector 200 such as depicted in FIGS. 2A-2B, however, the method may be applicable to other embodiments of the test strip port connectors described herein. At step 501, a top member 202 of the test strip port connector 200 is opened so that access may be had to an interior of the test strip port connector 200 to insert a test strip 206. One end of the test strip 206 is inserted into the test strip port connector 200, at step 502, and the top member 202 is closed on top of the inserted test strip 206, at step 503, which seals the interior of the test strip port connector 200 to prevent fluid ingress from a sample applied to the test strip 206. At step 504, a sample is applied to the test strip which is detected by the test meter 10 and an assay is performed on the sample as in the usual course.

As will be appreciated by one skilled in the art, aspects of the present invention may be embodied as a processing system, method, or apparatus. Accordingly, aspects of the present invention may take the form of an entirely hardware embodiment, an entirely software embodiment (including firmware, resident software, micro-code, etc.), or an embodiment combining software and hardware aspects that may all generally be referred to herein as a "circuit," "circuitry," "module," 'subsystem' and/or "system." Furthermore, aspects of the present invention may take the form of a computer program product embodied in one or more computer readable medium(s) having computer readable program code embodied thereon.

Program code and/or data representative of operations and measurements performed may be stored using any appropriate medium, including but not limited to any combination of one or more computer readable medium(s). A computer readable storage medium may be, for example, an electronic, magnetic, optical, electromagnetic, infrared, or semiconductor system, apparatus, or device, or any suitable combination of the foregoing. More specific examples of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible, non-transitory medium that can contain, or store a program for use by or in connection with an instruction execution system, apparatus, or device.

Program code and/or data representative of operations and measurements performed may be transmitted using any appropriate medium, including but not limited to wireless, wireline, optical fiber cable, RF, etc., or any suitable combination of the foregoing.

Parts List for FIGS. 1A-5
10 analyte meter
11 housing, meter
13 data port
14 display
16 user interface buttons
22 strip port connector opening
24 test strip
100 analyte measurement system
101 memory module
102 buttons/keypad module
103 user interface module
104 test strip port connector circuit
105 motor control module
106 transceiver module
107 antenna
108 WiFi module
109 Bluetooth module
110 NFC module
111 cell module
112 RAM module
113 ROM module
114 external storage
116 power supply module
117 AC power supply
118 battery power supply
119 display module
120 audio module
121 speaker
122 microcontroller (processing unit)
123 communication or power interface
125 test strip analyte module—analog front end
140 data management unit
200 test strip port connector
202 top member
203 top contact seal
204 bottom member
205 bottom contact seal
206 test strip
208 double-sided arrow
210 hinge
212 electrical contacts
214 arrow
216 contact pads
220 top side, test strip
221 bottom side, test strip
225 sample fluid
230 sample chamber (electrochemical cell)
300 test strip port connector, enclosed
302 motor
304 strip detector
400 test strip port connector
402 contact pad
403 contact seal
404 contact pad
405 entry slot
406 test strip
407 entry slot
410 arrow
411 hinge portion, top member
412 electrical contact, strip port connector
413 hinge portion, bottom member
414 electrical contact, strip port connector
420 assay position, test strip
429 sample chamber inlet
430 sample chamber
431 test strip slider
432 slider button
434 slider arm
436 slider arm
450 top member
451 bottom surface, top member
460 bottom member
461 top surface, bottom member
501 step—open test strip port connector
502 step—insert test strip into assay position
503 step—close test strip port connector
504 step—detect sample and perform assay While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An analyte test meter comprising:
a test strip port connector configured for receiving an analytical test strip, said port connector comprising at least one electrical contact for engaging at least one electrical contact pad of the received analytical test strip, the received analytical test strip further comprising a sample chamber for receiving a fluid sample; and
said port connector defining an interior and having a movable portion that permits a test strip to be inserted into the connector when the movable portion is moved to an open position, said connector further including at least one seal element configured for sealing the test strip port connector against ingress therein by the fluid sample, wherein the sealing mechanism is configured to be moved into a sealing position across the inserted test strip when the movable portion is moved to a closed position about the inserted test strip;

wherein movable portion is hingably connected to the port connector and is configured to be moved manually between the open and closed positions; and further comprising a motor configured for automatically moving the movable portion of the port connector between the open and closed positions.

2. A test meter comprising:

a test strip port connector comprising an electrical contact for engaging a contact pad of a first analytical test strip, the first analytical test strip comprising the contact pad at a first end thereof and a sample chamber at an opposite end thereof;

said port connector having a portion that is movable between an open position and a closed position for allowing access to an enclosure defined by the port connector wherein moving the movable portion to the closed position secures the test strip in engagement with the electrical contact and creates a fluidic seal to prevent ingress of fluid into the test meter;

a housing for storing the first analytical test strip therein; and a slider operable to insert the first analytical test strip from the housing into the test strip port connector and for engaging the electrical contact with the contact pad of the first analytical test strip.

3. The test meter of claim 2, further comprising a second analytical test strip stored in the housing together with the first analytical test strip, wherein the second analytical test strip is configured to be inserted from the housing into the test strip port connector using the slider.

4. A test meter comprising:

a test strip port connector comprising an electrical contact for engaging a contact pad of a first analytical test strip, the first analytical test strip comprising the contact pad at a first end thereof and a sample chamber at an opposite end thereof;

said port connector having a portion that is movable between an open position and a closed position for allowing access to an enclosure defined by the port connector wherein moving the movable portion to the closed position secures the test strip in engagement with the electrical contact and creates a fluidic seal to prevent ingress of fluid into the test meter; and wherein the port connector includes at least one seal element for said securing the test strip in engagement with the electrical contact and for sealing the electrical contact from the sample chamber;

wherein the test strip port connector comprises a first seal element disposed on an interior surface of the movable portion and a second seal element on an interior surface of a corresponding portion of the port connector such that moving the movable portion to the closed position causes the first and second seal elements to sealingly engage corresponding surfaces of an inserted test strip;

wherein the first and second seal elements are disposed directly opposite each other such that the first and second seal elements engage corresponding opposite surfaces of the inserted test strip when the movable portion is moved to the closed position; and wherein the movable portion is connected to the port connector by a hinge, and wherein the movable portion is moved into the open and closed positions by rotating the movable portion about the hinge; and further comprising a motor for said rotating the movable portion about the hinge.

5. The test meter of claim 4, wherein said first and second seal elements are made from a pliable rubber.

* * * * *